(12) United States Patent
Larsen

(10) Patent No.: US 10,538,522 B2
(45) Date of Patent: Jan. 21, 2020

(54) BRASSINOSTEROID MIMETICS

(71) Applicant: The Regents of the University of California, Oakland, CA (US)

(72) Inventor: Paul Brian Larsen, Riverside, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 15/573,090

(22) PCT Filed: May 13, 2016

(86) PCT No.: PCT/US2016/032538
§ 371 (c)(1),
(2) Date: Nov. 9, 2017

(87) PCT Pub. No.: WO2016/183519
PCT Pub. Date: Nov. 17, 2016

(65) Prior Publication Data
US 2018/0127421 A1 May 10, 2018

Related U.S. Application Data

(60) Provisional application No. 62/161,841, filed on May 14, 2015.

(51) Int. Cl.
*A01N 43/90* (2006.01)
*C07D 487/04* (2006.01)

(52) U.S. Cl.
CPC .......... *C07D 487/04* (2013.01); *A01N 43/90* (2013.01)

(58) Field of Classification Search
None
See application file for complete search history.

(56) References Cited

U.S. PATENT DOCUMENTS

| 4,139,705 A | 2/1979 | Dunbar et al. |
| 5,430,007 A | 7/1995 | Michaely et al. |
| 2014/0171326 A1 | 6/2014 | Borras Hidalgo et al. |
| 2015/0005167 A1 | 1/2015 | Jung et al. |

FOREIGN PATENT DOCUMENTS

WO 2010015849 A2 2/2010

OTHER PUBLICATIONS

Pubchem, CID 864621, Jul. 9, 2005, pp. 1-12 [online], [retrieved on May 7, 2016], Retrieved from the Internet <URL:https://pubchem.ncbi.nlm.nih.gov/compound/864621>; p. 3, formula.
Pubchem, CID 654052, Jun. 4, 2005, pp. 1-12 [online], [retrieved on May 7, 2016], Retrieved from the Internet <URL:https://pubchem.ncbi.nlm.nih.gov/compound/654052>; p. 3, formula.
Thomas, Shane, International Search Report and Written Opinion, United States Patent Application, PCT/US2016/032538, dated Aug. 5, 2016.
Wittmann-Regis, Agnes, International Preliminary Report on Patentability and Written Opinion, The International Bureau of WIPO, PCT/US2016/032538, dated Nov. 23, 2017.
Ismail et al., "Synthesis of Some New Biologically Active Sulfur Compounds Containing Pyrazolo[3,4-d] Pyrimidine Moiety", Phosphorus, Sulfur, and Silicon, 178:1795-1805, 2003.
Rufet, Jacques, Extended European Search Report, Application No. 16793651.7, European Patent Office, dated Jan. 16, 2019.
Starosotnikov et al., "Synthesis of peri-annelated heterocyclic systems based on 3-substituted 1-aryl-4, 6-dinitro-1H-indazoles", Russian Chemical Bulletin, International Edition, vol. 52, No. 8, pp. 1777-1781, Aug. 2003.

*Primary Examiner* — Alton N Pryor
(74) *Attorney, Agent, or Firm* — Gavrilovich, Dodd & Lindsey LLP

(57) ABSTRACT

The disclosure provides brassinosteroid mimetics and method of using such mimetics.

9 Claims, 4 Drawing Sheets

FIG. 2A-B

BRASSINOSTEROID MIMETICS

CROSS REFERENCE TO RELATED APPLICATIONS

This application is a U.S. National Stage Application filed under 35 U.S.C. § 371 and claims priority to International Application No. PCT/US2016/032538, filed May 13, 2016, which application claims priority to U.S. Provisional Application Ser. No. 62/161,841, filed May 14, 2015, the disclosures of which are incorporated herein by reference.

TECHNICAL FIELD

The disclosure provides methods and compositions for modulating brassinosteroid responsiveness, growth and fruit production in plants.

BACKGROUND

Brassinosteroids are plant hormones involved in multiple developmental processes. Brassinosteroids are involved in plant growth promotion, increase in the success of fertilization, shortening the period of vegetative growth, improvement of fruit quality, increase of stress resistance and improved crop yield.

Brassinosteroids are a group of naturally occurring polyhydroxy steroids. Natural brassinosteroids have a common 5-alpha cholestan skeleton and their structural variations come from the kind and orientation of functionalities on the skeleton, and from variations in the B ring. Brassinosteroids exert their activity by binding to the plasma membrane receptor kinase BRI1, resulting in the activation of a signaling pathway that involves a glycogen synthase kinase-3-like kinase (BIN2) and a serine/threonine phosphatase BSU1. BIN2 negatively regulates BR signaling by phosphorylation of the transcription factors BES1 (and probably the closely related BZR1), while dephosphorylation of BES1 by BSU1 activates the transcription of BR induced genes.

Due to their importance as plant growth promoting compounds, several companies developed production methods for brassinosteroids and analogues. Such methods have been disclosed, amongst others, in JP01075500, JP01175992 and U.S. Pat. No. 6,667,278.

SUMMARY

The disclosure provides brassinosteroid mimetics having the ability to increase plant growth and biomass, fruiting and improve resistance to infection and disease. In addition, the brassinosteroid mimetics may inhibit ethylene signaling in plants and in some embodiments, ethylene production.

The disclosure also provide formulation and delivery compositions comprising the brassinosteroid mimetics and methods of using such mimetics.

The disclosure provides a brassinosteroid mimetic comprising the structure of Formula I:

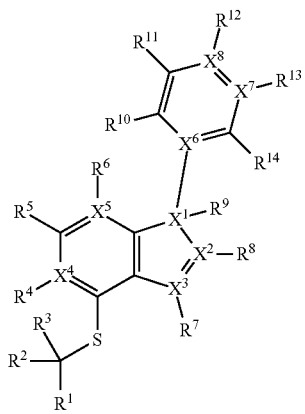

Formula I wherein, $X^1$-$X^8$ are independently selected from C or N; $R^1$ is selected from an alkyl-$R^{16}$, heteroalkyl-$R^{16}$, $NH_2$, $NR^{17}_2$, hydroxyl, ester, aldehyde, ketone, and carboxyl; $R^2$-$R^{14}$ are independently selected from H, D, $NH_2$, $NR^{17}_2$, —O-alkyl, —O-ether, SH, $SR^{17}$, optionally substituted alkyl, optionally substituted heteroalkyl, optionally substituted alkenyl, optionally substituted heteroalkenyl, optionally substituted alkynyl, optionally substituted heteroalkynyl, optionally substituted cycloalkyl, optionally substituted cycloalkenyl, optionally substituted aryl, optionally substituted heterocycle, hydroxyl, halo, imine, amide, nitro, nitroso, nitrile, isocyanate, ester, aldehyde, ketone, carboxyl, thiol, thionyl, sulfonyl, $SiR^{17}_3$, $PR^{17}_3$; and $R^{16}$ is selected from $NH_2$, hydroxyl, ester, aldehyde, ketone, and carboxyl; $R^{17}$ is selected from an optionally substituted ($C_1$-$C_6$)alkyl, an optionally substituted hetero-($C_1$-$C_6$)alkyl, an optionally substituted ($C_1$-$C_6$)alkenyl, an optionally substituted hetero-($C_1$-$C_6$)alkenyl, an optionally substituted ($C_1$-$C_6$)alkynyl, or an optionally substituted hetero-($C_1$-$C_6$)alkynyl, a cycloalkyl, an aryl, and a heterocycle, and wherein $R^4$, $R^6$-$R^9$, $R^{12}$, and $R^{13}$ are absent if bound to an X that is an N. In one embodiment, the mimetic comprises the structure of Formula I(a):

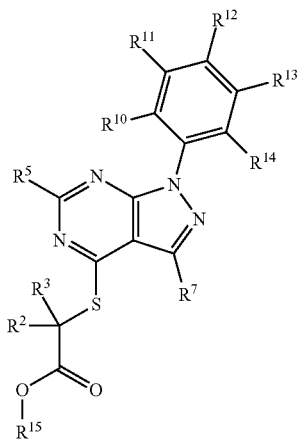

Formula I(a)

wherein, $R^2$, $R^3$, $R^5$, $R^7$, $R^{10}$-$R^{14}$ are independently selected from H, D, $NH_2$, —O-alkyl, —O-ether, SH, optionally substituted ($c_1$-$C_{12}$)alkyl, optionally substituted hetero($c_1$-$C_{12}$)alkyl, optionally substituted ($c_2$-$C_{12}$)alkenyl, optionally substituted hetero($c_2$-$C_{12}$)alkenyl, optionally substituted ($c_2$-$C_{12}$)alkynyl, optionally substituted hetero($c_2$-$C_{12}$)alkynyl, optionally substituted cycloalkyl, optionally substituted cycloalkenyl, optionally substituted aryl, optionally substituted heterocycle, hydroxyl, halo, imine, amide, nitro, nitroso, nitrile, isocyanate, ester, aldehyde, ketone, carboxyl, thiol, thionyl, and sulfonyl; and $R^{15}$ is an optionally substituted $(C_1-C_6)$alkyl, an optionally substituted hetero-$(C_1-C_6)$alkyl, an optionally substituted $(C_1-C_6)$alkenyl, an optionally substituted hetero-$(C_1-C_6)$alkenyl, an optionally substituted $(C_1-C_6)$alkynyl, or an optionally substituted hetero-$(C_1-C_6)$alkynyl, a cycloalkyl, an aryl, and a heterocycle. In another embodiment, the mimetic comprises the structure of Formula I(a):

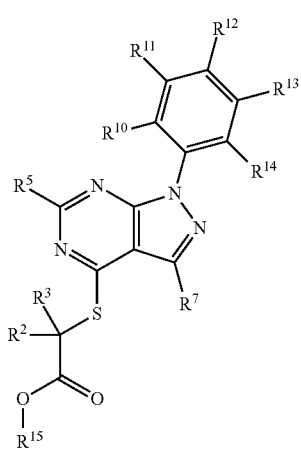

Formula I(a)

wherein, $R^2$ and $R^3$ are independently selected from H, D, optionally substituted $(c_1-C_6)$alkyl, optionally substituted hetero$(c_1-C_6)$alkyl, optionally substituted $(c_2-C_6)$alkenyl, and optionally substituted hetero$(c_2-C_6)$alkenyl; $R^5$, $R^7$, $R^{10}$-$R^{14}$ are independently selected from H, D, $NH_2$, $NR^{17}_2$, —O-alkyl, —O-ether, SH, $SR^{16}$, optionally substituted $(c_1-C_{12})$alkyl, optionally substituted hetero$(c_1-C_{12})$alkyl, optionally substituted $(c_2-C_{12})$alkenyl, optionally substituted hetero$(c_2-C_{12})$alkenyl, optionally substituted $(c_2-C_{12})$alkynyl, optionally substituted hetero$(c_2-C_{12})$alkynyl, optionally substituted cycloalkyl, optionally substituted cycloalkenyl, optionally substituted aryl, optionally substituted heterocycle, hydroxyl, halo, imine, amide, nitro, nitroso, nitrile, isocyanate, ester, aldehyde, ketone, carboxyl, thiol, thionyl, and sulfonyl; and $R^{15}$ an optionally substituted $(C_1-C_6)$alkyl and an aryl. In still another embodiment, the mimetic comprises the structure of any one of the following:

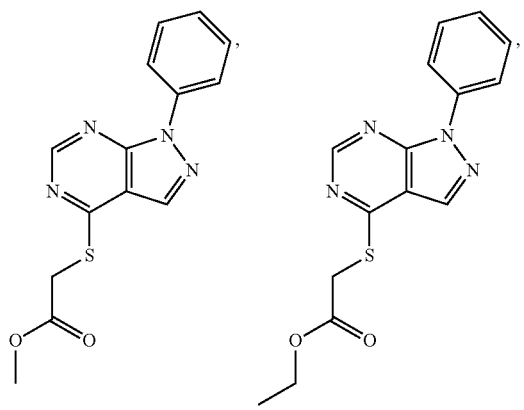

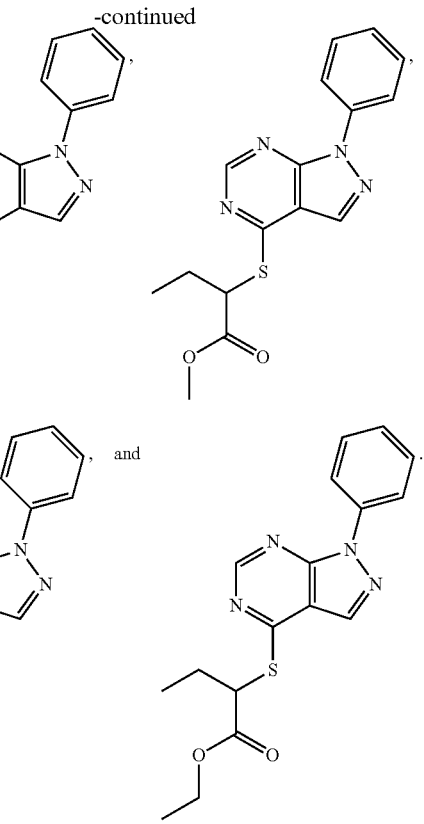

The disclosure also provides a method to activate the brassinosteroid response in a plant, comprising applying a mimetic of the disclosure to the plant or in the root zone of the plant.

The disclosure also provides a composition for promoting plant growth comprising a brassinosteroid mimetic of the disclosure in a suitable delivery vehicle. In one embodiment, the composition further comprises a formulating agent.

The disclosure also provides a method of promoting plant growth by applying to a plant an effective amount of a composition of the disclosure.

The disclosure provides a method of promoting a desired tissue morphology and/or physiological state in a higher plant, wherein said desired tissue morphology or physiological state is selected from at least one of: shoot growth, grain, seed or fruit yield enhancement, root (radicle) growth retardation, improved fruit set and fruit quality or other desired tissue morphology or physiological state that is promoted by a brassinosteroid, the method comprising applying an effective amount of a brassinosteroid mimetic of the disclosure. In one embodiment, the brassinosteroid mimetic is applied in conjunction with a plant growth regulator and an appropriate formulating agent.

BRIEF DESCRIPTION OF THE DRAWINGS

The accompanying drawings, which are incorporated into and constitute a part of this specification, illustrate one or more embodiments of the disclosure and, together with the detailed description, serve to explain the principles and implementations of the invention.

DETAILED DESCRIPTION

Figure 1:
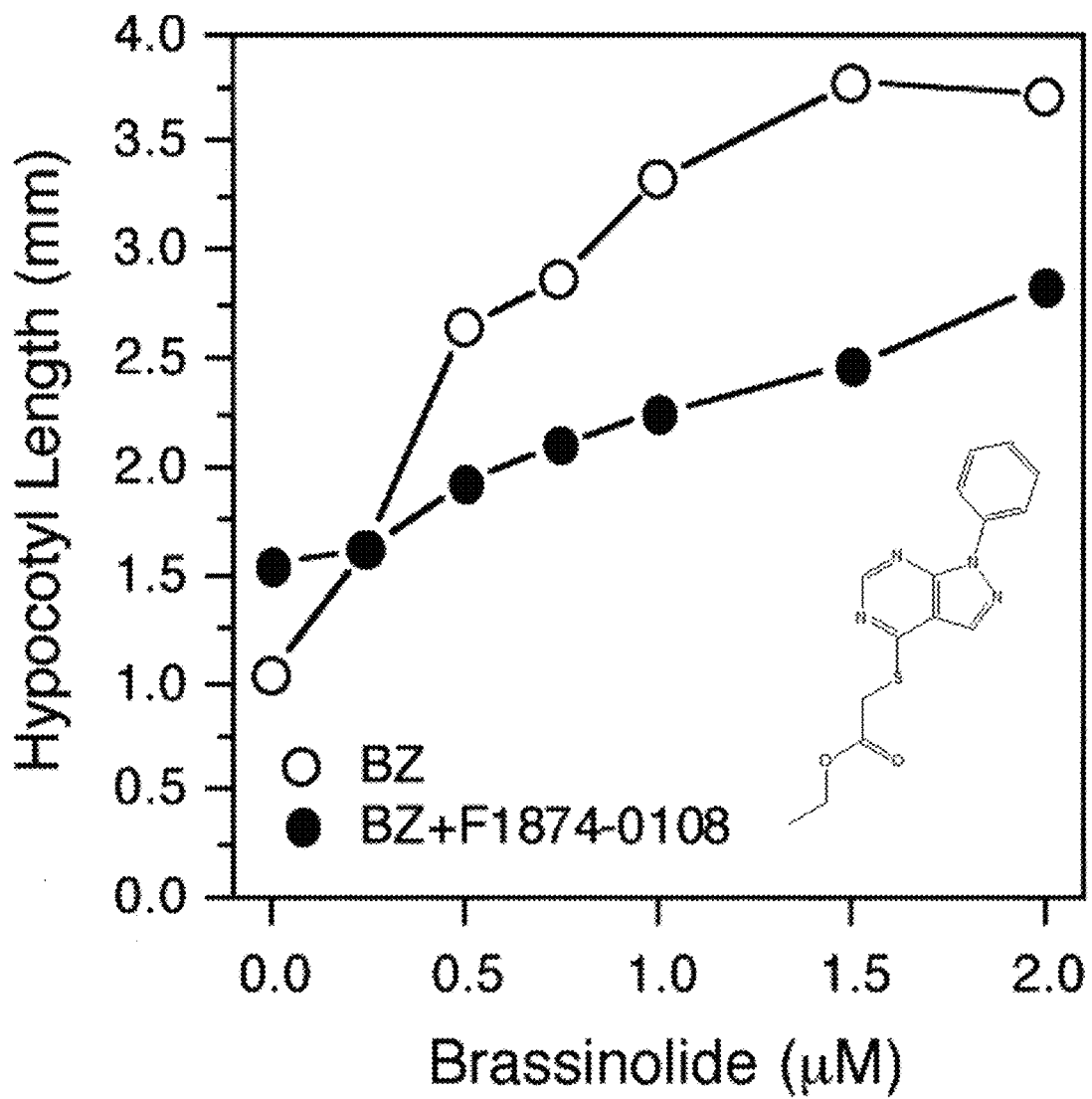
FIG. 1 shows hypocotyl length in response to the presence of a brassinosteroid mimetic of the disclosure.
Figure 2:
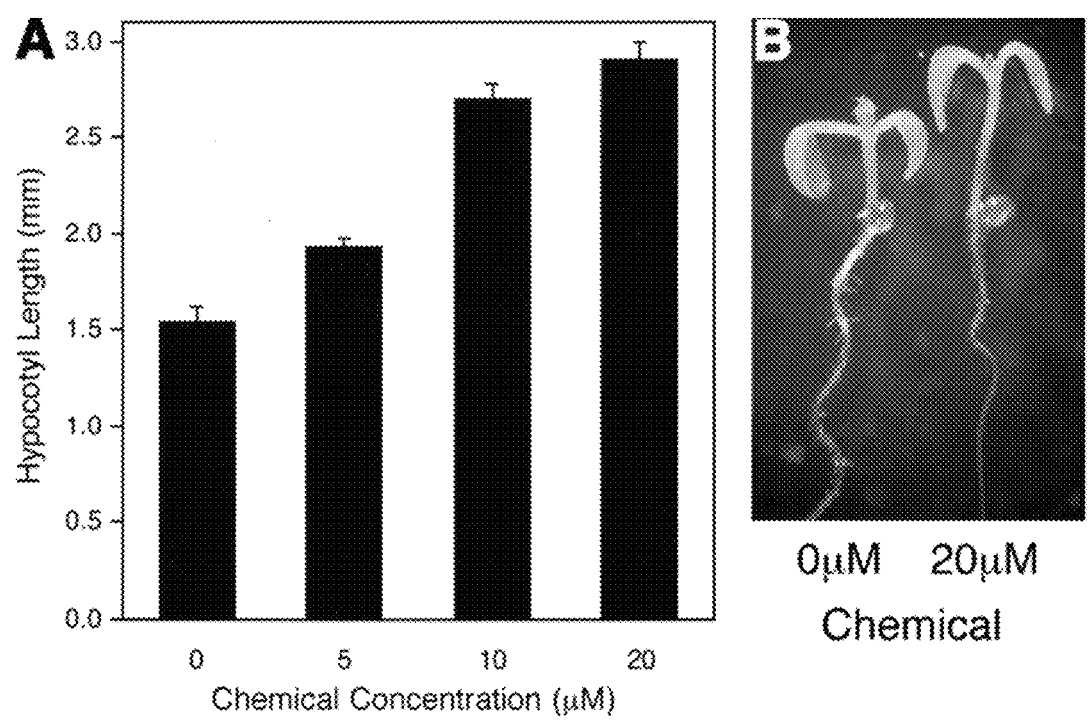
FIG. 2A-B shows seedling growth in the presence of a brassinosteroid mimetic. (A) *Arabidopsis* seedlings were grown for 7 days in light in the presence of increasing concentrations of a brassinosteroid mimetic of the disclosure. (B) a photo of seedlings grown at 0 and 20 μM of brassinosteroid mimetic.
Figure 3:
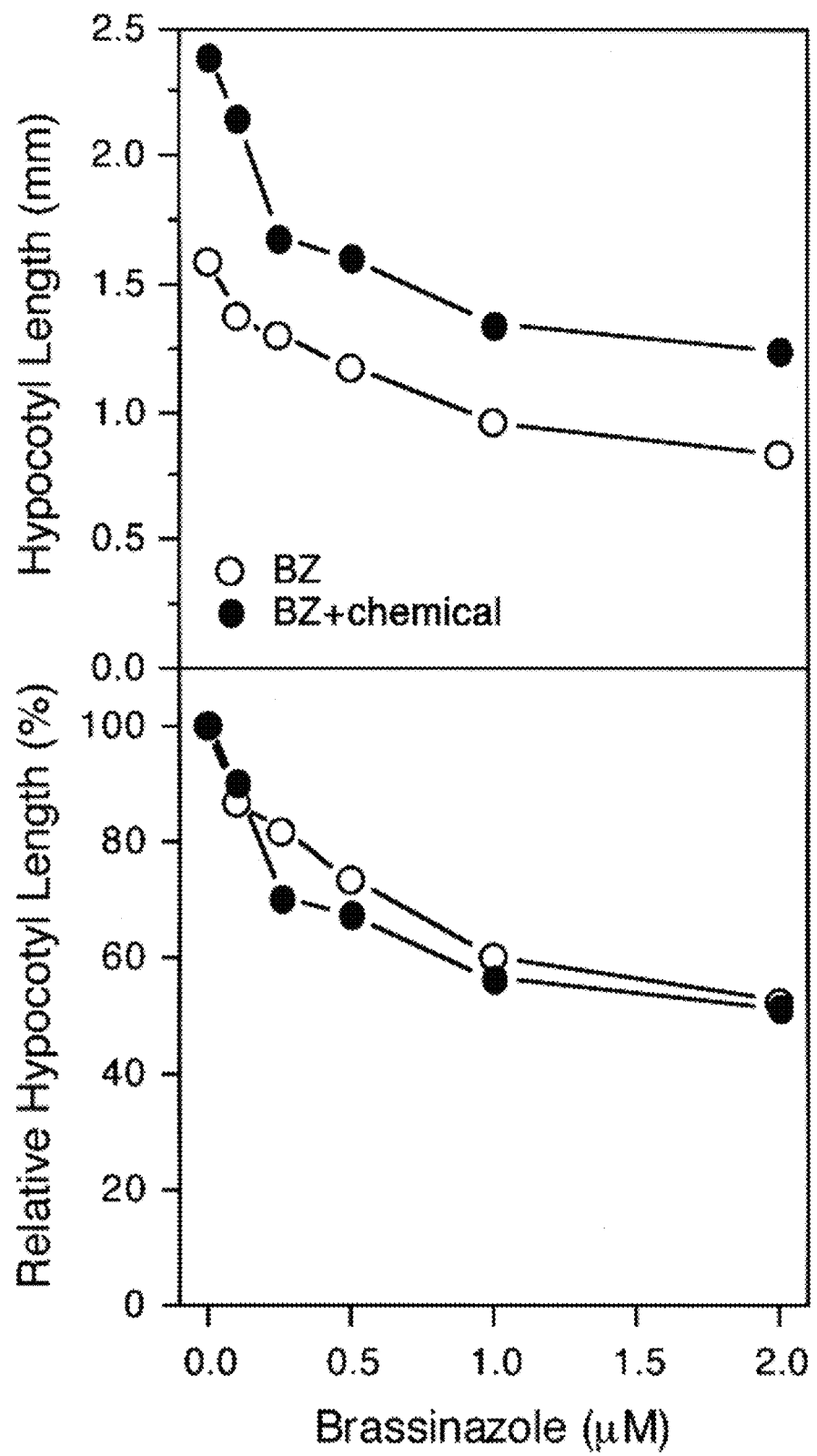
FIG. 3 shows the effect of inhibitors of brassinosteroid synthesis in the presence and absence of a brassinosteroid mimetic of the disclosure. Seedlings were treated with an inhibitor of BR synthesis (brassinazole; (BZ)). Treatment with BZ results in shortening of the hypocotyls since BR is required for cell elongation. Addition of BZ+the chemical results in hypocotyl lengths that track the hypocotyl lengths of BZ alone suggesting that the brassinosteroid mimetic is enhancing what little remains of BR in the seedling after BZ treatment. This is not consistent with what is seen for Bikinin, which is a constitutive activator of BR signaling and would be independent of BR synthesis (i.e. treatment with BZ would not result in inhibition of hypocotyl length in the presence of BZ).
Figure 4:
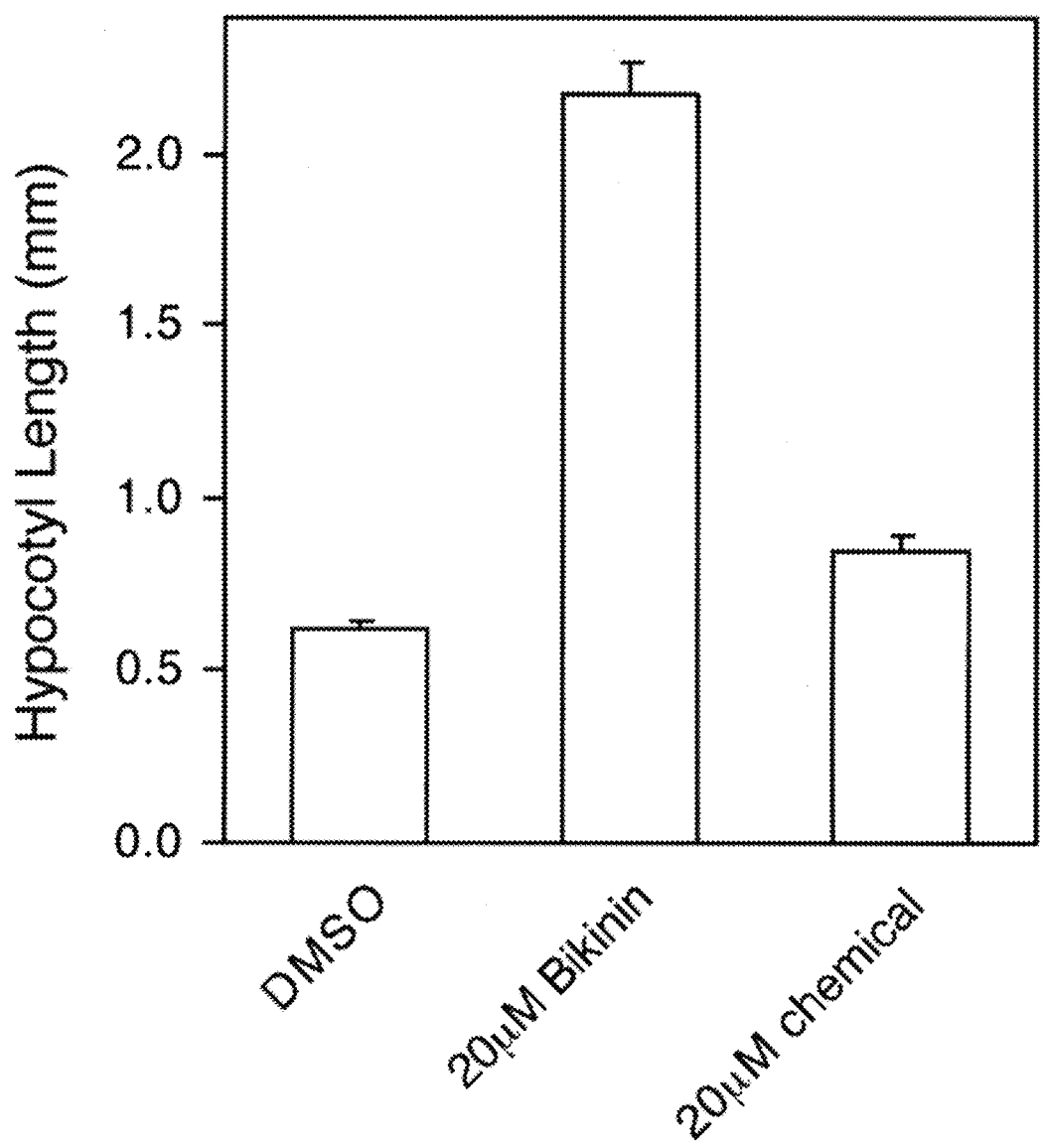
FIG. 4 shows the effect of a brassinosteroid mimetic in a mutant seedling. Growth of a mutant that has a mutational defect in the brassinosteroid receptor BRI1 is compared when treated with a mimetic of the disclosure and Bikinin, which constitutively activates BIN2, and which results in promotion of long hypocotyls independent of BR. Treatment of bri1-6 results in failure to activate the BR pathway and indicates that the mimetic is indeed working differently than Bikinin even though they both are likely targeting the same component of the BR pathway, BIN2.

As used herein and in the appended claims, the singular forms "a," "and," and "the" include plural referents unless the context clearly dictates otherwise. Thus, for example, reference to "a mimetic" includes a plurality of such mimetics and reference to "the plant" includes reference to one or more plants and equivalents thereof.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Brassinosteroids control plant size, with loss of brassinosteroid response leading to severely dwarfed and sterile plants. Additionally, brassinosteroids are critically important to plant responses to infection and stresses along with progression of developmental phenomena such as fruit ripening.

The term "mimetic" refers to a brassinosteroid analogue which possesses statistically significant brassinosteroid activity.

The term "non-steroidal" refers to compounds lacking the 17-carbon fused tetracyclic structure characteristic of steroids. In some embodiments, the mimetics of the disclosure can be considered non-steroidal brassinosteroid mimetics.

Brassinosteroid mimetics of the disclosure were identified by screening for compounds that block ethylene response in *Arabidopsis*. The brassinosteroid mimetics identified herein were found to prevent several outcomes of ethylene signaling and chosen for further study.

The method identified brassinosteroid mimetics having general Formula I:

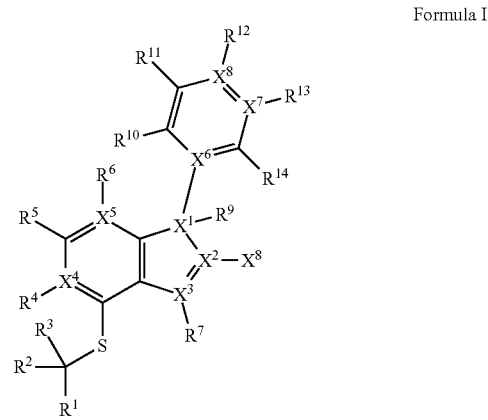

Formula I wherein, $X^1$-$X^8$ are independently selected from C or N; $R^1$ is selected from an alkyl-$R^{16}$, heteroalkyl-$R^{16}$, $NH_2$, $NR^{17}_2$, hydroxyl, ester, aldehyde, ketone, and carboxyl; $R^2$-$R^{14}$ are independently selected from H, D, $NH_2$, $NR^{17}_2$, —O-alkyl, —O-ether, SH, $SR^{17}$, optionally substituted alkyl, optionally substituted heteroalkyl, optionally substituted alkenyl, optionally substituted heteroalkenyl, optionally substituted alkynyl, optionally substituted heteroalkynyl, optionally substituted cycloalkyl, optionally substituted cycloalkenyl, optionally substituted aryl, optionally substituted heterocycle, hydroxyl, halo, imine, amide, nitro, nitroso, nitrile, isocyanate, ester, aldehyde, ketone, carboxyl, thiol, thionyl, sulfonyl, $SiR^{17}_3$, $PR^{17}_3$; and $R^{16}$ is selected from $NH_2$, hydroxyl, ester, aldehyde, ketone, and carboxyl; $R^{17}$ is selected from an optionally substituted ($C_1$-$C_6$)alkyl, an optionally substituted hetero-($C_1$-$C_6$)alkyl, an optionally substituted ($C_1$-$C_6$)alkenyl, an optionally substituted hetero-($C_1$-$C_6$)alkenyl, an optionally substituted ($C_1$-$C_6$)alkynyl, or an optionally substituted hetero-($C_1$-$C_6$)alkynyl, a cycloalkyl, an aryl, and a heterocycle, and wherein $R^4$, $R^6$-$R^9$, $R^{12}$, and $R^{13}$ are absent if bound to an X that is an N.

In certain embodiments, the brassinosteroid mimetic comprises formula I(a):

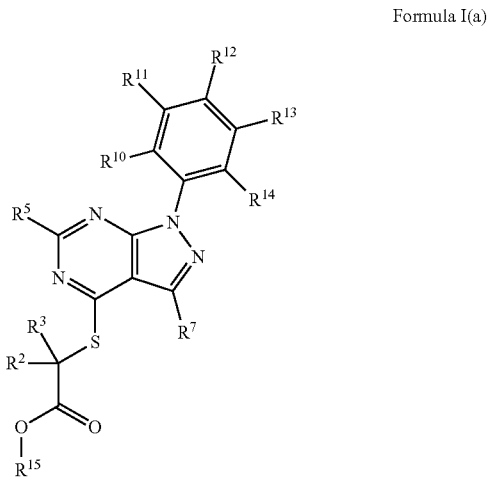

Formula I(a)

wherein, $R^2$, $R^3$, $R^5$, $R^7$, $R^{10}$-$R^{14}$ are independently selected from H, D, $NH_2$, —O-alkyl, —O-ether, SH, optionally substituted ($c_1$-$C_{12}$)alkyl, optionally substituted hetero($c_1$-$C_{12}$)alkyl, optionally substituted ($c_2$-$C_{12}$)alkenyl, optionally substituted hetero($c_2$-$C_{12}$)alkenyl, optionally substituted ($c_2$-$C_{12}$)alkynyl, optionally substituted hetero($c_2$-$C_{12}$)alkynyl, optionally substituted cycloalkyl, optionally substituted cycloalkenyl, optionally substituted aryl, optionally substituted heterocycle, hydroxyl, halo, imine, amide, nitro, nitroso, nitrile, isocyanate, ester, aldehyde, ketone, carboxyl, thiol, thionyl, and sulfonyl; and $R^{15}$ is an optionally substituted ($C_1$-$C_6$)alkyl, an optionally substituted hetero-($C_1$-$C_6$)alkyl, an optionally substituted ($C_1$-$C_6$)alkenyl, an optionally substituted hetero-($C_1$-$C_6$)alkenyl, an optionally substituted ($C_1$-$C_6$)alkynyl, or an optionally substituted hetero-($C_1$-$C_6$)alkynyl, a cycloalkyl, an aryl, and a heterocycle. In still a further embodiment, $R^2$ and $R^3$ are independently selected from H, D, optionally substituted ($c_1$-$C_6$)alkyl, optionally substituted hetero($c_1$-$C_6$)alkyl, optionally substituted ($c_2$-$C_6$)alkenyl, and optionally substituted hetero ($c_2$-$C_6$)alkenyl; $R^5$, $R^7$, $R^{10}$-$R^{14}$ are independently selected from H, D, $NH_2$, $NR^{17}_2$, —O-alkyl, —O-ether, SH, $SR^{16}$, optionally substituted ($c_1$-$C_{12}$)alkyl, optionally substituted hetero ($c_1$-$C_{12}$)alkyl, optionally substituted ($c_2$-$C_{12}$)alkenyl, optionally substituted hetero($c_2$-$C_{12}$)alkenyl, optionally substituted ($c_2$-$C_{12}$)alkynyl, optionally substituted hetero($c_2$-$C_{12}$)alkynyl, optionally substituted cycloalkyl, optionally substituted cycloalkenyl, optionally substituted aryl, optionally substituted heterocycle, hydroxyl, halo, imine, amide, nitro, nitroso, nitrile, isocyanate, ester, aldehyde, ketone, carboxyl, thiol, thionyl, and sulfonyl; and $R^{15}$ an optionally substituted ($C_1$-$C_6$)alkyl and an aryl.

In certain specific embodiments, the brassinosteroid mimetic comprises:

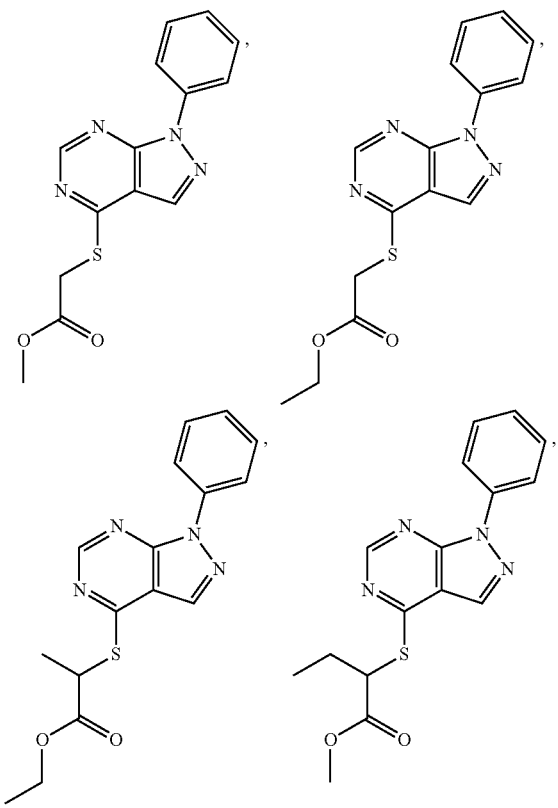

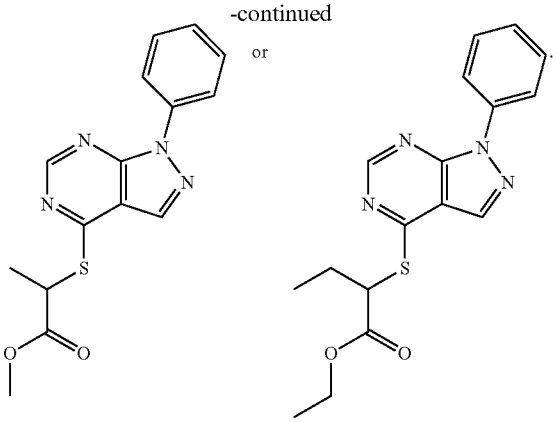

Subsequent analysis of the brassinosteroid mimetics revealed that it produced growth characteristics associated with response to brassinosteroids even though the chemical does not resemble either brassinosteroids or precursors to brassinosteroids. Growth studies to look at the effects of the chemical on brassinosteroid phenomena show that the brassinosteroid mimetics boost brassinosteroid response by upwards of 80% in a brassinosteroid dependent manner.

The brassinosteroid mimetics of the disclosure were tested and shown to block ethylene response by hyperactivating brassinosteroid signaling. The application of any one of the brassinosteroid mimetics of the disclosure, which are all closely related, results in massive increases in plant size. This phenomena is believed to be due to the mimetic hyperactivating brassinosteroid response since plants that are insensitive to brassinosteroids do not have this hyperactivation. Additionally, reduction of internal concentrations of brassinosteroids by inhibition of brassinosteroid biosynthesis reduces the effects of the mimetic on growth. In FIG. 1, one can see the promotive effects of F1874-0108 (inset), a brassinosteroid mimetic of the disclosure, on plant height, with chemical treated plants being almost 100% taller than untreated plants. Hyperactivation of brassinosteroid signaling represents an effective means to increase plant biomass and increase the capability of plants with regard to disease resistance and other brassinosteroid regulated phenomena.

In FIG. 1, brassinosteroid production was limited by addition of brassinazole (BZ, which is a chemical inhibitor of brassinosteroid biosynthesis). Subsequently, if one adds a brassinosteroid mimetic (e.g., F1874-0108) to the seedlings without adding exogenous brassinosteroids (i.e. brassinolide), the mimetic treated seedlings are substantially longer than those that are just BZ treated. This is because BZ does not completely block brassinosteroid production and mimetic amplifies the limited amount of brassinosteroid signaling that is present because BIN2 is not fully inhibited. Interestingly, as one compensates for the loss of brassinosteroid production by adding back exogenous brassinosteroids in the form of brassinolide, the length of BZ seedlings goes up by almost 400%. In stark contrast, addition of brassinolide plus mimetic severely curtails this burst in growth because mimetic prevents the full inhibition of BIN2.

In other words, BIN2 is a key negative regulator of brassinosteroid response (i.e., when it is off, brassinosteroid response is on; when it is on, brassinosteroid response is off). The data show that mimetic (e.g., a brassinosteroid mimetic of the disclosure) holds BIN2 in a state that prevents it from being fully on or fully off. This makes the brassinosteroid mimetics of the disclosure both an activator of brassinosteroid response and an inhibitor of BIN2 when there is too much brassinosteroids. Bikinin completely shuts off BIN2 and results in strong activation of brassinosteroid response regardless of whether brassinosteroids are present or not. The mimetics of the disclosure provide flexibility in regulating this response thereby providing a chemical niche.

Consequently, the brassinosteroid mimetics of the disclosure enhance the activity of normal levels of endogenous brassinosteroids and prevents the severe effects of high levels of brassinosteroids. In contrast, bikinin treatment would result in brassinosteroid responses that would be maximally increased independently of brassinosteroid levels in the plant.

The disclosure provides methods and compositions for (i) promoting plant growth, (ii) promoting fruit development, (iii) increasing plant biomass and (iv) inhibiting auxin and ethylene signaling in a plant comprising contacting a plant, plant part, tissue, flower, fruit and the like with a brassinosteroid mimetic comprising a structure of formula I:

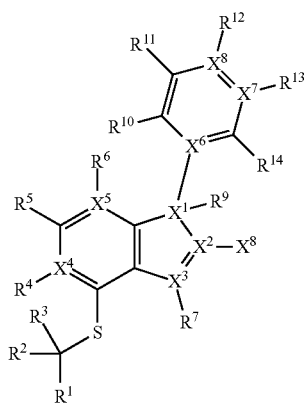

Formula I wherein, $X^1$-$X^8$ are independently selected from C or N; $R^1$ is selected from an alkyl-$R^{16}$, heteroalkyl-$R^{16}$, $NH_2$, $NR^{17}_2$, hydroxyl, ester, aldehyde, ketone, and carboxyl; $R^2$-$R^{14}$ are independently selected from H, D, $NH_2$, $NR^{17}_2$, —O-alkyl, —O-ether, SH, $SR^{17}$, optionally substituted alkyl, optionally substituted heteroalkyl, optionally substituted alkenyl, optionally substituted heteroalkenyl, optionally substituted alkynyl, optionally substituted heteroalkynyl, optionally substituted cycloalkyl, optionally substituted cycloalkenyl, optionally substituted aryl, optionally substituted heterocycle, hydroxyl, halo, imine, amide, nitro, nitroso, nitrile, isocyanate, ester, aldehyde, ketone, carboxyl, thiol, thionyl, sulfonyl, $SiR^{17}_3$, $PR^{17}_3$; and $R^{16}$ is selected from $NH_2$, hydroxyl, ester, aldehyde, ketone, and carboxyl; $R^{17}$ is selected from an optionally substituted $(C_1$-$C_6)$alkyl, an optionally substituted hetero-$(C_1$-$C_6)$alkyl, an optionally substituted $(C_1$-$C_6)$alkenyl, an optionally substituted hetero-$(C_1$-$C_6)$alkenyl, an optionally substituted $(C_1$-$C_6)$alkynyl, or an optionally substituted hetero-$(C_1$-$C_6)$alkynyl, a cycloalkyl, an aryl, and a heterocycle, and wherein $R^4$, $R^6$-$R^9$, $R^{12}$, and $R^{13}$ are absent if bound to an X that is an N.

In one embodiment, the brassinosteroid mimetic comprises the structure of Formula I(a):

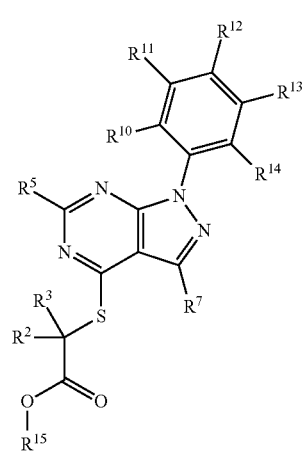

Formula I(a)

wherein, $R^2$, $R^3$, $R^5$, $R^7$, $R^{10}$-$R^{14}$ are independently selected from H, D, $NH_2$, —O-alkyl, —O-ether, SH, optionally substituted $(c_1$-$C_{12})$alkyl, optionally substituted hetero$(c_1$-$C_{12})$alkyl, optionally substituted $(c_2$-$C_{12})$alkenyl, optionally substituted hetero$(c_2$-$C_{12})$alkenyl, optionally substituted $(c_2$-$C_{12})$alkynyl, optionally substituted hetero$(c_2$-$C_{12})$alkynyl, optionally substituted cycloalkyl, optionally substituted cycloalkenyl, optionally substituted aryl, optionally substituted heterocycle, hydroxyl, halo, imine, amide, nitro, nitroso, nitrile, isocyanate, ester, aldehyde, ketone, carboxyl, thiol, thionyl, and sulfonyl; and $R^{15}$ is an optionally substituted $(C_1$-$C_6)$alkyl, an optionally substituted hetero-$(C_1$-$C_6)$alkyl, an optionally substituted $(C_1$-$C_6)$alkenyl, an optionally substituted hetero-$(C_1$-$C_6)$alkenyl, an optionally substituted $(C_1$-$C_6)$alkynyl, or an optionally substituted hetero-$(C_1$-$C_6)$alkynyl, a cycloalkyl, an aryl, and a heterocycle.

In another embodiment, the brassinosteroid mimetic comprises the structure of Formula I(a):

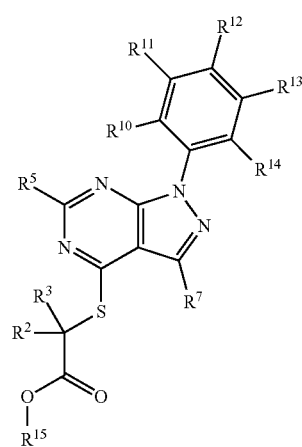

Formula I(a)

wherein, $R^2$ and $R^3$ are independently selected from H, D, optionally substituted $(c_1$-$C_6)$alkyl, optionally substituted hetero$(c_1$-$C_6)$alkyl, optionally substituted $(c_2$-$C_6)$alkenyl, and optionally substituted hetero$(c_2$-$C_6)$alkenyl; $R^5$, $R^7$, $R^{10}$-$R^{14}$ are independently selected from H, D, $NH_2$, $NR^{17}_2$, —O-alkyl, —O-ether, SH, $SR^{16}$, optionally substituted $(c_1$-

$C_{12}$)alkyl, optionally substituted hetero($c_1$-$C_{12}$)alkyl, optionally substituted ($c_2$-$C_{12}$)alkenyl, optionally substituted hetero($c_2$-$C_{12}$)alkenyl, optionally substituted ($c_2$-$C_{12}$)alkynyl, optionally substituted hetero($c_2$-$C_{12}$)alkynyl, optionally substituted cycloalkyl, optionally substituted cycloalkenyl, optionally substituted aryl, optionally substituted heterocycle, hydroxyl, halo, imine, amide, nitro, nitroso, nitrile, isocyanate, ester, aldehyde, ketone, carboxyl, thiol, thionyl, and sulfonyl; and $R^{15}$ an optionally substituted ($C_1$-$C_6$)alkyl and an aryl.

In still a further embodiment, the brassinosteroid mimetic comprises the structure of any one of the following:

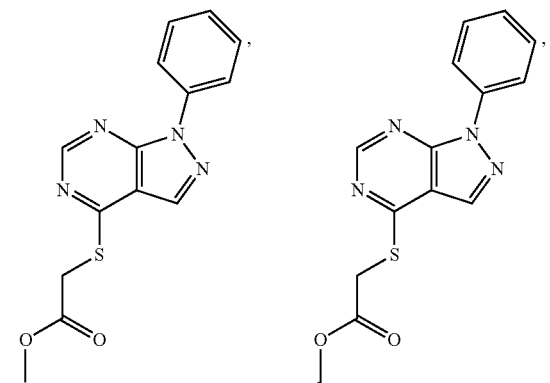

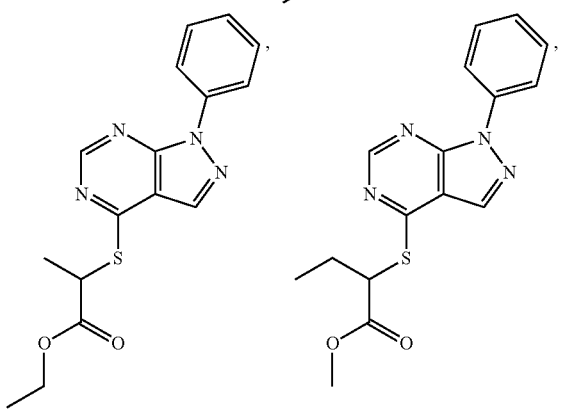

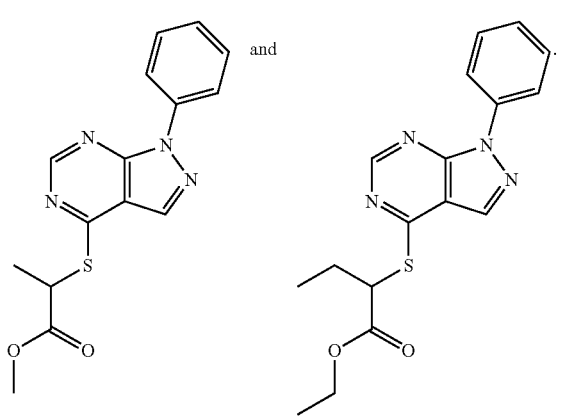

In one embodiment, the brassinosteroid mimetic comprises the structure of any one of the following:

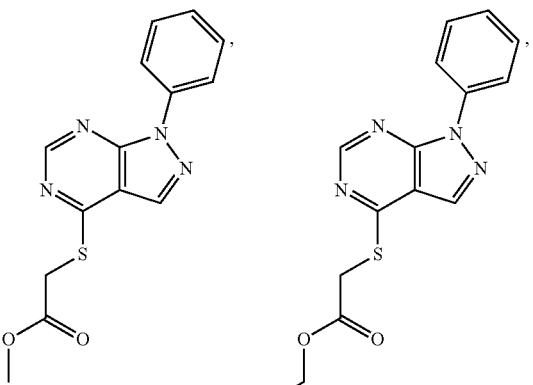

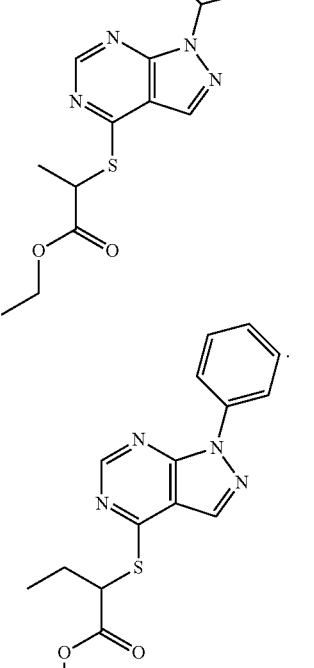

In one embodiment, any of the foregoing brassinosteroid mimetics (e.g., of Formula I, I(a) etc.) have a biological activity selected from the group consisting of (i) stimulating plant growth, (ii) increasing plant biomass, (iii) increasing fruit size, (iv) increasing fruit development, (v) improving plant resistance to stress and disease and (vi) blocking ethylene response.

For example, in addition to being an agonist of brassinosteroid activity, the brassinosteroid mimetic of the disclosure can provide a method of inhibiting ethylene production or auxin induced gene expression in a plant comprising contacting the plant with a brassinosteroid mimetic.

The disclosure provides a method of inhibiting senescence due to ethylene production in a plant comprising contact the plant with a brassinosteroid mimetic.

The disclosure also provides compositions useful in the methods of the disclosure.

Methods are provided for (i) modulating ethylene signaling and/or auxin induced gene expression in a plant or inhibiting ethylene production and/or (ii) increasing plant growth, flowering, fruit development and size, improving plant resistance to stress and disease and the like comprising applying or contacting a plant with an effective amount of a composition comprising brassinosteroid mimetic as set forth herein. "Effective amount" is intended to mean an amount sufficient to cause the desired biological activity.

The methods and compositions of the disclosure can be employed to modify a variety plant characteristics or activities such as, for example, plant growth, plant size, fruit growth, fruit size, the ripening and/or senescence of flowers, fruits, and vegetables; abscission of foliage, flowers, and fruit; the life of ornamentals such as potted plants, cut flowers, shrubbery, seeds, and dormant seedlings; auxin activity, terminal growth, apical dominance, branching, tillering, morphology of plants, modifying and improving resistance or susceptibility to plant pathogens such as fungi, changing bio-chemical compositions of plants, abortion or inhibition of flowering and seed development, lodging effects, seed germination and dormancy, and hormone or epinasty effects.

The compositions of the disclosure include a brassinosteroid mimetic and may further include a surface-active agent, an inert carrier, a preservative, a humectant, a feeding stimulant, an attractant, an encapsulating agent, a binder, an emulsifier, a dye, a UV protective, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular plants. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the disclosure are normally applied in the form of compositions and can be applied to the crop area, plant, or seed to be treated or in the case of cuttings (e.g., cut flowers) to the water. For example, the compositions of the disclosure may be applied during growth, seeding or storage.

The brassinosteroid mimetic of the disclosure may be applied simultaneously or in succession with other compounds. Methods of applying a composition of the disclosure include, but are not limited to, foliar application, seed coating, and soil or water application. The number of applications and the rate of application depend on the particular purpose and plant (e.g., to preserve cut flowers, of inhibit fruit spoilage).

Suitable surface-active agents include, but are not limited to, anionic compounds such as a carboxylate of, for example, a metal; carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions of the disclosure can be in a suitable form for direct application or as a concentrate of primary composition that requires dilution with a suitable quantity of water or other diluent before application. The concentration of brassinosteroid mimetic will vary depending upon the nature of the particular formulation, specifically, whether it is a concentrate or to be used directly.

A composition of the disclosure can be applied to the environment of a plant, for example, spraying, atomizing, dusting, scattering, coating or pouring, introducing into or on the soil, introducing into irrigation water, by seed treatment or general application or dusting. The compositions of the disclosure can conveniently contain an insecticide if this is thought necessary.

The brassinosteroid mimetics described can promote growth and development of higher plants and enhances the crop yield of horticultural, agricultural, floricultural and forestry plants as would be expected from the application of a brassinosteroid. Beneficial effects of the brassinosteroid mimetics described herein include promoting a desired tissue morphology and/or physiological state in a higher plant wherein such desired tissue morphology or physiological state is promoted by a brassinosteroid. Such beneficial effects may include growth promotion, enhanced crop quality, and increased resistance to disease, herbicides, bactericides, insecticides, low temperature or high temperature stress, and moisture stress.

It is also contemplated that the brassinosteroid mimetics described herein can be used in mammalian subjects. For example, the disclosure contemplates the use of a brassinosteroid mimetic of the disclosure to increase whole-body anabolic activity in a subject comprising administering to the subject a therapeutically effective amount of a composition comprising a brassinosteroid mimetic of the disclosure. In another embodiment, the disclosure contemplates the use of a brassinosteroid mimetic in a pharmaceutical formulation for treating an androgen-associated condition selected from benign prostatic hyperplasia and androgenic alopecia. In still another embodiment, the brassinosteroid mimetics can be used to inhibit hyperproliferation in mammalian cells, for treating proliferative diseases in mammals, and for regulation of the adverse effects of steroid dysfunctions in mammalian cells and mammals.

As used herein, the term "plant" refers to either a whole plant, a plant part, a plant cell, or a group of plant cells, such as plant tissue, for example. Plantlets are also included within the meaning of "plant". Plants include flowering, decorative plants, agricultural plant and the like.

Examples of monocotyledonous plants include, but are not limited to, asparagus, field and sweet corn, barley, wheat, rice, sorghum, onion, pearl millet, rye and oats. Examples of dicotyledonous plants include, but are not limited to tomato, tobacco, cotton, potato, rapeseed, field beans, soybeans, peppers, lettuce, peas, alfalfa, clover, cole crops or *Brassica oleracea* (e.g., cabbage, broccoli, cauliflower, brussels sprouts), radish, carrot, beets, eggplant, spinach, cucumber, squash, melons, cantaloupe, sunflowers and various ornamentals. Woody species include poplar, pine, sequoia, cedar, oak, etc.

A number of embodiments of the invention have been described. Nevertheless, it will be understood that various modifications may be made without departing from the spirit and scope of the invention. Accordingly, other embodiments are within the scope of the following claims.

What is claimed is:

1. A method to activate the brassinosteroid response in a plant, comprising applying a compound of Formula I(a) to the plant or in the root zone of the plant, wherein Formula I(a) comprises:

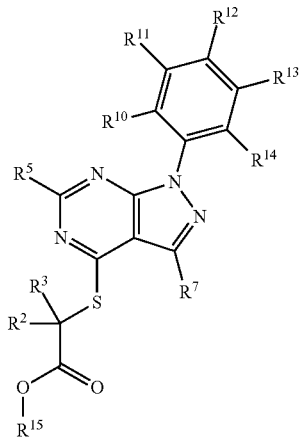

Formula I(a)

wherein,
$R^2$, $R^3$, $R^5$, $R^7$, $R^{10}$-$R^{14}$ are independently selected from H, D, $NH_2$, —O-alkyl, —O-ether, SH, optionally substituted ($c_1$-$C_{12}$)alkyl, optionally substituted hetero($C_1$-$C_{12}$)alkyl, optionally substituted ($C_2$-$C_{12}$)alkenyl, optionally substituted hetero($C_2$-$C_{12}$)alkenyl, optionally substituted ($C_2$-$C_{12}$)alkynyl, optionally substituted hetero($C_2$-$C_{12}$)alkynyl, optionally substituted cycloalkyl, optionally substituted cycloalkenyl, optionally substituted aryl, optionally substituted heterocycle, hydroxyl, halo, imine, amide, nitro, nitroso, nitrile, isocyanate, ester, aldehyde, ketone, carboxyl, thiol, thionyl, and sulfonyl; and $R^{15}$ is an optionally substituted ($C_1$-$C_6$)alkyl, an optionally substituted hetero-($C_1$-$C_6$)alkyl, an optionally substituted ($C_2$-$C_6$)alkenyl, an optionally substituted hetero-($C_2$-$C_6$)alkenyl, an optionally substituted ($C_2$-$C_6$)alkynyl, or an optionally substituted hetero-($C_1$-$C_6$)alkynyl, a cycloalkyl, an aryl, and a heterocycle.

2. A composition for promoting plant growth comprising a brassinosteroid mimetic as set forth in Formula I(a) in a suitable delivery vehicle, wherein Formula I(a) comprises:

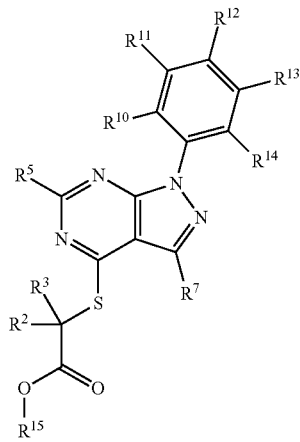

Formula I(a)

wherein,
$R^2$, $R^3$, $R^5$, $R^{10}$-$R^{14}$ are independently selected from H, D, $NH_2$, —O-alkyl, —O-ether, SH, optionally substituted ($c_1$-$C_{12}$)alkyl, optionally substituted hetero ($C_1$-$C_{12}$)alkyl, optionally substituted ($C_2$-$C_{12}$)alkenyl, optionally substituted hetero($C_2$-$C_{12}$)alkenyl, optionally substituted ($C_2$-$C_{12}$)alkynyl, optionally substituted hetero($C_2$-$C_{12}$)alkynyl, optionally substituted cycloalkyl, optionally substituted cycloalkenyl, optionally substituted aryl, optionally substituted heterocycle, hydroxyl, halo, imine, amide, nitro, nitroso, nitrile, isocyanate, ester, aldehyde, ketone, carboxyl, thiol, thionyl, and sulfonyl;

$R^7$ is selected from D, $NH_2$—O-alkyl, —O-ether, SH, optionally substituted ($c_1$-$C_{12}$)alkyl, optionally substituted hetero($C_1$-$C_{12}$)alkyl, optionally substituted ($C_2$-$C_1$)alkenyl, optionally substituted hetero($C_2$-$C_1$)alkenyl, optionally substituted ($C_2$-$C_1$)alkynyl, optionally substituted hetero($C_2$-$C_1$)alkynyl, optionally substituted cycloalkyl, optionally substituted cycloalkenyl, optionally substituted aryl, optionally substituted heterocycle, hydroxyl, halo, imine, amide, nitro, nitroso, nitrile, isocyanate, ester, aldehyde, ketone, carboxyl, thiol, thionyl, and sulfonyl; and $R^{15}$ is an optionally substituted ($C_1$-$C_6$)alkyl, an optionally substituted hetero-($C_1$-$C_6$)alkyl, an optionally substituted ($C_1$-$C_6$)alkenyl, an optionally substituted hetero-($C_1$-$C_6$)alkenyl, an optionally substituted ($C_1$-$C_6$)alkynyl, or an optionally substituted hetero-($C_1$-$C_6$)alkynyl, a cycloalkyl, an aryl, and a heterocycle.

3. The composition of claim 2 further comprising a formulating agent.

4. A method of promoting plant growth by applying to a plant an effective amount of the composition of claim 2.

5. A method of promoting a desired tissue morphology and/or physiological state in a higher plant, wherein said desired tissue morphology or physiological state is selected from at least one of: shoot growth, grain, seed or fruit yield enhancement, root (radicle) growth retardation, improved fruit set and fruit quality or other desired tissue morphology or physiological state that is promoted by a brassinosteroid, the method comprising applying to the plant an effective amount of a brassinosteroid mimetic of Formula I(a):

Formula I(a)

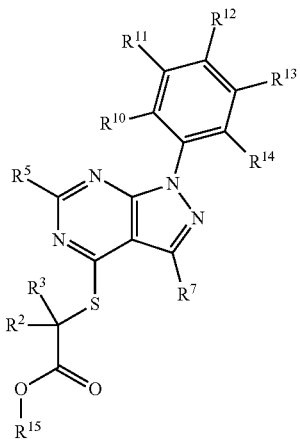

Formula I(a)

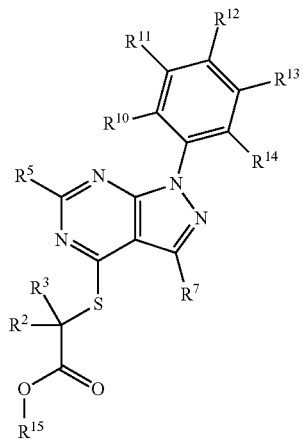

wherein, $R^2$, $R^3$, $R^5$, $R^7$, $R^{10}$-$R^{14}$ are independently selected from H, D, $NH_2$, —O-alkyl, —O-ether, SH, optionally substituted ($C_1$-$C_{12}$)alkyl, optionally substituted hetero($C_1$-$C_{12}$)alkyl, optionally substituted ($C_2$-$C_{12}$) alkenyl, optionally substituted hetero($C_2$-$C_{12}$)alkenyl, optionally substituted ($C_2$-$C_{12}$)alkynyl, optionally substituted hetero($C_2$-$C_{12}$)alkynyl, optionally substituted cycloalkyl, optionally substituted cycloalkenyl, optionally substituted aryl, optionally substituted heterocycle, hydroxyl, halo, imine, amide, nitro, nitroso, nitrile, isocyanate, ester, aldehyde, ketone, carboxyl, thiol, thionyl, and sulfonyl; and $R^{15}$ is an optionally substituted ($C_1$-$C_6$)alkyl, an optionally substituted hetero-($C_1$-$C_6$)alkyl, an optionally substituted ($C_2$-$C_6$)alkenyl, an optionally substituted hetero-($C_2$-$C_6$)alkenyl, an optionally substituted ($C_2$-$C_6$) alkynyl, or an optionally substituted hetero-($C_1$-$C_6$) alkynyl, a cycloalkyl, an aryl, and a heterocycle.

6. The method of claim 5 wherein the brassinosteroid mimetic is applied in conjunction with a plant growth regulator and a formulating agent.

7. A composition for promoting plant growth comprising a brassinosteroid mimetic as set forth in Formula I(a) in a suitable delivery vehicle, wherein Formula I(a) comprises:

wherein, $R^2$, $R^3$, $R^5$, $R^7$, $R^{10}$-$R^{14}$ are independently selected from H, D, $NH_2$, —O-alkyl, —O-ether, SH, optionally substituted ($c_1$-$C_{12}$)alkyl, optionally substituted hetero($C_1$-$C_{12}$)alkyl, optionally substituted ($C_2$-$C_{12}$) alkenyl, optionally substituted hetero($C_2$-$C_{12}$)alkenyl, optionally substituted ($C_2$-$C_{12}$)alkynyl, optionally substituted hetero($C_2$-$C_{12}$)alkynyl, optionally substituted cycloalkyl, optionally substituted cycloalkenyl, optionally substituted aryl, optionally substituted heterocycle, hydroxyl, halo, imine, amide, nitro, nitroso, nitrile, isocyanate, ester, aldehyde, ketone, carboxyl, thiol, thionyl, and sulfonyl; and $R^{15}$ is an optionally substituted hetero-($C_1$-$C_6$)alkyl, an optionally substituted ($C_2$-$C_6$)alkenyl, an optionally substituted hetero-($C_2$-$C_6$)alkenyl, an optionally substituted ($C_2$-$C_6$)alkynyl, or an optionally substituted hetero-($C_2$-$C_6$)alkynyl, a cycloalkyl, an aryl, and a heterocycle.

8. The composition of claim 7 further comprising a formulating agent.

9. A method of promoting plant growth by applying to a plant an effective amount of the composition of claim 7.

\* \* \* \* \*